(12) United States Patent
Malinowski et al.

(10) Patent No.: US 9,618,525 B2
(45) Date of Patent: Apr. 11, 2017

(54) MODULE FOR A LABORATORY SAMPLE DISTRIBUTION SYSTEM, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Michal Malinowski, Backnang (DE); Henny Volz, Bietigheim-Bissingen (DE); Christian Riether, Muehltal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/865,822

(22) Filed: Sep. 25, 2015

(65) Prior Publication Data
US 2016/0097786 A1    Apr. 7, 2016

(30) Foreign Application Priority Data
Oct. 7, 2014 (EP) .................................... 14187891

(51) Int. Cl.
G01N 35/04 (2006.01)
B65G 54/02 (2006.01)
G01N 35/00 (2006.01)

(52) U.S. Cl.
CPC ............ *G01N 35/04* (2013.01); *B65G 54/02* (2013.01); *G01N 35/00* (2013.01); *B65G 2201/0261* (2013.01); *G01N 2035/00326* (2013.01); *G01N 2035/0477* (2013.01)

(58) Field of Classification Search
None
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |

(Continued)

FOREIGN PATENT DOCUMENTS

| | | |
|---|---|---|
| CN | 201045617 Y | 4/2008 |
| CN | 102109530 A | 6/2011 |

(Continued)

OTHER PUBLICATIONS

International Search Report issued Dec. 12, 2012, in Application No. PCT/EP2012/071751, 4 pages.

*Primary Examiner* — Jill Warden
*Assistant Examiner* — Benjamin Whatley
(74) *Attorney, Agent, or Firm* — Roche Diagnostics Operations, Inc.

(57) ABSTRACT

A module for a laboratory sample distribution system, a laboratory sample distribution system comprising such modules, and a laboratory automation system comprising such a laboratory sample distribution system are presented. A magnetic coupling enhancer is provided in order to increase magnetic coupling between adjacent modules.

18 Claims, 6 Drawing Sheets

(56) References Cited

U.S. PATENT DOCUMENTS

| | | |
|---|---|---|
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,281,888 B2 | 10/2012 | Bergmann |
| 8,796,186 B2 | 8/2014 | Shirazi |
| 9,211,543 B2 | 12/2015 | Ohga et al. |
| 9,239,335 B2 | 1/2016 | Heise et al. |
| 2002/0009391 A1 | 1/2002 | Marquiss et al. |
| 2003/0089581 A1 | 5/2003 | Thompson et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1* | 8/2014 | Heise .................... B65G 54/02 414/749.2 |
| 2014/0234949 A1 | 8/2014 | Wasson et al. |
| 2014/0234978 A1* | 8/2014 | Heise .................... B65G 54/02 436/48 |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |

FOREIGN PATENT DOCUMENTS

| | | |
|---|---|---|
| DE | 3909786 A1 | 9/1990 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2502675 A1 | 9/2012 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 03-192013 A | 8/1991 |
| JP | H05-69350 A | 3/1993 |
| JP | H05-180847 A | 7/1993 |
| JP | 06-26808 A | 4/1994 |
| JP | 06-148198 A | 5/1994 |
| JP | 6-156730 A | 6/1994 |

(56) References Cited

FOREIGN PATENT DOCUMENTS

| | | |
|---|---|---|
| JP | 06-211306 A1 | 8/1994 |
| JP | 07-228345 A | 8/1995 |
| JP | 07-236838 A | 9/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-062188 A | 3/2009 |
| JP | 2009-145188 A | 7/2009 |
| JP | 2009-300402 A | 12/2009 |
| JP | 2013-172009 A | 9/2013 |
| JP | 2013-172009 A | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

MODULE FOR A LABORATORY SAMPLE DISTRIBUTION SYSTEM, LABORATORY SAMPLE DISTRIBUTION SYSTEM AND LABORATORY AUTOMATION SYSTEM

CROSS-REFERENCE TO RELATED APPLICATIONS

This application claims priority to EP 14187891.8, filed Oct. 7, 2014, which is hereby incorporated by reference.

BACKGROUND

The present disclosure generally relates to a module for a laboratory sample distribution system, to a laboratory sample distribution system comprising such a module, and to a laboratory automation system comprising such a laboratory sample distribution system.

Known laboratory sample distribution systems are typically used in laboratory automation systems in order to distribute or to transport samples contained in sample containers between different laboratory stations. Such a laboratory sample distribution system provides for a high throughput and for reliable operation.

It has been found that such a laboratory sample distribution system can be assembled out of a plurality of modules, wherein the modules can be put together in order to arrive at a desired shape and size of a transport plane of the resulting laboratory sample distribution system.

However, this is a need for a module for a laboratory sample distribution system with improved magnetic coupling between such modules, for a laboratory sample distribution system comprising such modules, and for a laboratory automation system comprising such a laboratory sample distribution system.

SUMMARY

According to the present disclosure, a module for a laboratory sample distribution system, to a laboratory sample distribution system comprising such a module, and to a laboratory automation system comprising such a laboratory sample distribution system is presented. The module can comprise a transport plane to support sample container carriers. Each sample container carrier can comprises at least one magnetically active device. The module can further comprise a plurality of electro-magnetic actuators stationary arranged below the transport plane. The electro-magnetic actuators can move the sample container carriers on top of the transport plane by applying a magnetic force to the sample container carriers. Each electro-magnetic actuator can comprise a ferromagnetic core. Adjacent ferromagnetic cores can be magnetically coupled to each other by respective magnetic coupling elements. The module can further comprise a magnetic coupling enhancer for increasing magnetic coupling to adjacent modules. The magnetic coupling enhancer can comprise a plurality of magnetic coupling protrusions, each magnetic coupling protrusion can be positioned between an outer edge of the module and a corresponding ferromagnetic core of an electro-magnetic actuator positioned adjacent to the outer edge, and/or a plurality of contact surfaces. The contact surfaces can be contacted by a corresponding number of magnetic coupling rods.

Accordingly, it is a feature of the embodiments of the present disclosure to provide a module for a laboratory sample distribution system with improved magnetic coupling between such modules, a laboratory sample distribution system comprising such modules, and a laboratory automation system comprising such a laboratory sample distribution system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A module for a laboratory sample distribution system is presented. The module can comprise a transport plane to support sample container carriers. Each sample container carrier can comprise at least one magnetically active device. It can be noted that the transport plane can also be denoted as a transport surface. It can further be noted that it can also be said that the transport plane or transport surface can carry the sample container carriers.

The module can further comprise a plurality of electro-magnetic actuators stationary arranged below the transport plane. The electro-magnetic actuators can move sample container carriers on top of the transport plane by applying a magnetic force to the sample container carriers. Each electro-magnetic actuator can comprise a ferromagnetic core. Adjacent ferromagnetic cores can be magnetically coupled to each other by magnetic coupling elements.

The magnetic coupling elements can be embodied as bars or otherwise shaped elements made of magnetic, especially ferromagnetic, material. The magnetic coupling elements can increase magnetic coupling between the ferromagnetic cores and thus can increase magnetic field strengths that are used to drive the sample container carriers. Thus, the magnetic coupling elements can increase energy efficiency of the module.

The module can further comprise magnetic coupling enhancers for increasing magnetic coupling to and between ferromagnetic cores of adjacent modules. The magnetic coupling enhancers can be implemented as follows.

The magnetic coupling enhancer may comprise a plurality of magnetic coupling protrusions. Each magnetic coupling protrusion can be positioned between an outer edge of the module and a corresponding ferromagnetic core of an electro-magnetic actuator positioned adjacent to the outer edge. The outer edge of a module can be an edge determining a border line to another module. Typically, the outer edge can be determined by a border line of the transport plane of a respective module. Typically, the module can have four outer edges forming a rectangular shape. Such a magnetic coupling protrusion can increase magnetic coupling to a neighboring module, because it can typically face towards the neighboring module. Magnetic coupling can be increased when the neighboring module has a corresponding protrusion such that a distance between the two protrusions can be minimized. The magnetic coupling enhancers or the magnetic coupling protrusions may be part of (or may belong to) the magnetic coupling elements.

The magnetic coupling enhancer may comprise a plurality of contact surfaces located at ferromagnetic cores of electro-magnetic actuators positioned adjacent to the outer edge of the module, or located at respective magnetic coupling elements of the electro-magnetic actuators positioned adjacent to the outer edge of the module, or located at respective magnetic coupling protrusions. The contact surfaces can be contacted by a corresponding plurality of magnetic coupling rods. This embodiment can allow for providing increased magnetic coupling by placing magnetic rods between the contact surfaces. By use of such an embodiment, it can be possible to couple ferromagnetic cores located adjacent to outer edges of neighboring modules without a gap. In this case, the number of rods equals the number of contact surfaces per module. Alternatively, it can be possible that a single rod can extend along the outer edge of the module and thereby can contact several contact surfaces. The magnetic coupling enhancers or the contact surfaces may be part of (or may belong to) the magnetic coupling elements.

According to one embodiment, each magnetic coupling protrusion can comprise a magnetic coupling surface positioned at the outer edge of the module and facing towards a surrounding of the module. The magnetic coupling surfaces can be arranged to magnetically couple to a further magnetic coupling surface of a neighboring module. In other words, when two modules are put together, two magnetic coupling surfaces can be positioned adjacent to each other and face each other so that a gap between the surfaces can be minimized. This can be achieved by arrangement of the magnetic coupling protrusions perpendicular to an outer edge of the module, and by arrangement of the magnetic coupling surface parallel to the outer edge. This can lead to a specifically high magnetic coupling.

According to one embodiment, each magnetic coupling surface can have a cross-section area larger than a cross-section area of the magnetic coupling elements. Especially, the magnetic coupling surfaces can have at least twice the cross-section area of the magnetic coupling elements. Increasing of the cross-section area of the magnetic coupling surfaces can increase magnetic coupling between ferromagnetic cores of different modules. Increasing the magnetic coupling surface relative to the cross-section area of the magnetic coupling elements can take into account that magnetic coupling between ferromagnetic cores of different modules can typically be decreased by a gap between the magnetic coupling surfaces. Increasing the area of the magnetic coupling surface can compensate this effect at least partially.

According to one embodiment, a plurality of positions can be defined on the module in a chequered manner. Each electro-magnetic actuator can be located on one such position such that in each second line of positions, each second position can be left blank. This arrangement of electro-magnetic actuators has been proven suitable for typical applications of the laboratory sample distribution system. For example, lines in which an electro-magnetic actuator is present at each position can be used as paths on which sample container carriers can move. Neighboring lines with less electro-magnetic actuators can provide for a certain distance between the paths.

According to one embodiment, the module can have four outer edges forming a rectangular shape. Electro-magnetic actuators can be located on each position along two of the four edges located perpendicular to each other. Furthermore, electro-magnetic actuators can be located on each second position along two further edges of the four edges. This embodiment can allow for a theoretically unlimited concatenation of modules to form a laboratory sample distribution system. If the modules are concatenated such that a line adjacent to an outer edge having an electro-magnetic actuator at each position can adjoin a line on an adjacent module having an electro-magnetic actuator at each second position, the pattern of electro-magnetic actuators formed over the whole common transport plane extending over all modules cannot be disturbed by a border between two modules.

According to one embodiment, the ferromagnetic cores, the magnetic coupling elements between those ferromagnetic cores, and the magnetic coupling enhancers of each line or some lines of positions having no blanks can be formed as a single ferromagnetic bar. This can significantly simplify assembly of such a module.

According to one embodiment, the module can comprise a first set of ferromagnetic bars and a second set of ferromagnetic bars. The ferromagnetic bars of the first set can be arranged parallel to each other and the ferromagnetic bars of the second set can be arranged parallel to each other. The ferromagnetic bars of the first set can be perpendicular to the ferromagnetic bars of the second set. When the bars are placed appropriately during assembly of the module, the ferromagnetic cores, the magnetic coupling elements and the magnetic coupling enhancers can be formed by the bars.

According to one embodiment, the ferromagnetic bars each can have recesses arranged such that the recesses of the ferromagnetic bars of the first set can be complementary to the recesses of the ferromagnetic bars of the second set. The ferromagnetic bars can be arranged such that corresponding complementary recesses can abut each other. This can allow for a specific simplification in assembly of the module. Typically, one bar of two bars abutting each other at a recess can have a ferromagnetic core extending upwards.

According to one embodiment, the ferromagnetic bars can each be formed out of a transformer sheet or out of a group of parallel transformer sheets electrically isolated to each other. Such a configuration has been proven useful for typical applications. Especially, a cheap and magnetically suitable material can be used. Using a plurality of transformer sheets electrically isolated to each other can, in particular, minimize eddy currents in the sheets. Thus, a parasitic resistance and corresponding heat generation can be minimized.

According to one embodiment, the magnetic coupling protrusions can be formed out of iron sheets. They can also be formed out of transformer sheets. This has been proven suitable for typical applications.

According to one embodiment, the ferromagnetic cores, the magnetic coupling elements, the magnetic coupling enhancers, the ferromagnetic bars and/or the transformer sheets can be formed out of magnetically high permeable material. This has been proven useful for typical applications because coupling of magnetic fields is significantly enhanced. This increases energy efficiency of the modules and hence energy efficiency of the laboratory sample distribution system.

A laboratory sample distribution system is presented. The laboratory sample distribution system can be implemented as follows. The laboratory sample distribution system may comprise a plurality of sample container carriers to carry one or more sample containers. Each sample container carrier can comprise at least one magnetically active device.

The laboratory sample distribution system can comprise a plurality of modules as described above. It can be noted that all variations and embodiments as discussed above can be used in the laboratory sample distribution system, as long as magnetic coupling protrusions are present. Discussed advantages can apply accordingly.

The modules can be arranged adjacent to each other such that magnetic coupling protrusions of neighboring modules can face each other and that the transport planes of the modules can form a common transport plane to support the sample container carriers. This can allow for an easy and efficient scaling of the laboratory sample distribution system by using an appropriate plurality of modules arranged in a specific way in order to resemble an intended shape of the common transport plane.

The laboratory sample distribution system can further comprise a control device to control the movement of the sample container carriers on top of the common transport plane by driving the electro-magnetic actuators of the modules such that the sample container carries can move along corresponding transport paths. This can allow for a central controlling of the sample container carriers such that they can execute certain transport tasks, for example to distribute or to transport sample containers containing blood samples or other medical samples to and from laboratory stations. The control device can control movement of the sample container carriers on the common transport plane in two dimensions. This can allow for a higher flexibility.

By use of the laboratory sample distribution system just described, energy efficiency of the laboratory sample distribution system comprising several modules can be significantly increased because magnetic coupling between neighboring modules can be increased as described above with reference to the modules.

In the following, a second way to implement the laboratory sample distribution system is described. It can be based on modules having contact surfaces. The laboratory sample distribution system can comprise a plurality of magnetic coupling rods positioned and fixed between two neighboring contact surfaces of respective different modules. This can increase magnetic coupling between neighboring modules in order to increase energy efficiency of the laboratory sample distribution system. Typically, the number of rods can equal the number of contact surfaces per module. Alternatively, it can be possible that a single rod can extend along the outer edge of the module and thereby contact several contact surfaces.

The rods can provide for an increased coupling between respective neighboring modules. The rods can even be exchanged one by one and they can be retrofitted in an already existing laboratory sample distribution system in order to increase energy efficiency.

According to one embodiment, the laboratory sample distribution system can comprise a retaining frame. The retaining frame can retain the plurality of modules from a bottom side of the modules. The bottom side of the modules can be opposite to the common transport plane. The plurality of magnetic coupling rods can be detachably fixed by a plurality of springs, especially coil springs, extending from the retaining frame to the rods. The contact surfaces may be located at bottom sides of ferromagnetic cores of electro-magnetic actuators positioned adjacent to the outer edge of the module, or located at bottom sides of respective magnetic coupling elements of the electro-magnetic actuators positioned adjacent to the outer edge of the module or located at bottom sides of respective magnetic coupling protrusions. This can allow for a simple detaching and attaching of the magnetic coupling rods in case one of the modules should be replaced.

According to one embodiment, each magnetic coupling rod can have a rectangular cross-section. The contact surfaces may be parallel to the common transport plane and located at bottom sides as mentioned above. Then the rods can be easily provided from the bottom to the contact surfaces.

A laboratory automation system can comprise a plurality of pre-analytical, analytical and/or post-analytical (laboratory) stations, and a laboratory sample distribution system as described above to distribute or to transport the sample container carriers and/or sample containers between the stations. The stations may be arranged adjacent to the laboratory sample distribution system.

Pre-analytical stations may perform any kind of pre-processing of samples, sample containers and/or sample container carriers. Analytical stations may use a sample or part of the sample and a reagent to generate a measuring signal. The measuring signal can indicate if and in which concentration, if any, an analyte exists. Post-analytical stations may perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Figure 1:
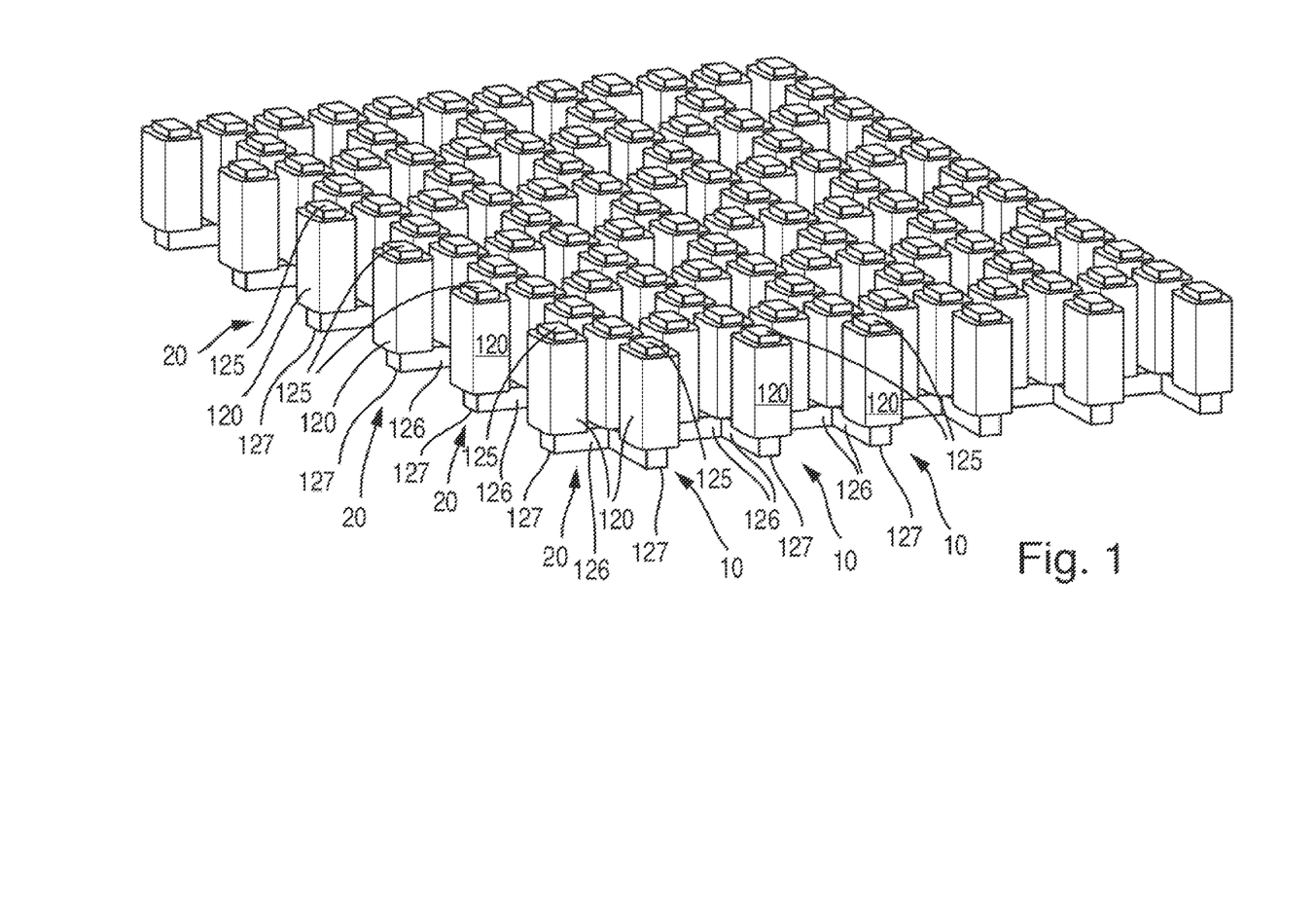
FIG. 1 illustrates a part of a module for a laboratory sample distribution system according to a first embodiment of the present disclosure.

Referring initially to FIG. 1, FIG. 1 shows a part of a module for a laboratory sample distribution system according to a first embodiment. It can be noted that typical parts of such a module such as a transport plane or a supporting structure are not shown in FIG. 1.

A plurality of electro-magnetic actuators 120 that can comprise electro-magnetic coils can be arranged in a configuration such that a field of positions can be defined in a chequered manner. In each second line of positions, each second position can be left blank.

Each electro-magnetic actuator 120 can comprise a ferromagnetic core 125. The ferromagnetic core 125 can increase a magnetic field generated by a respective electromagnetic coil of the electro-magnetic actuator 120.

Between ferromagnetic cores 125 of neighboring electro-magnetic actuators 120, a respective magnetic coupling element 126 can be arranged. The magnetic coupling elements 126 can increase magnetic coupling between respective pairs of ferromagnetic cores 125.

The electro-magnetic actuators 120 can drive sample container carriers on a transport plane (not shown) that can typically be positioned above the electro-magnetic actuators 120. By use of the magnetic coupling elements 126, energy efficiency of the module can be enhanced because the respective cores 125 of neighboring electro-magnetic actuators 120 can be magnetically coupled.

The ferromagnetic cores 125 and the magnetic coupling elements 126 that can be arranged along a line extending from the front side to the rear side as shown in FIG. 1 can be embodied as respective first ferromagnetic bars 10. Correspondingly, the ferromagnetic cores 125 and the magnetic coupling elements 126 arranged in lines perpendicular to that direction, i.e., from the left to the right side in FIG. 1, with the exception of ferromagnetic cores 125 already belonging to the first ferromagnetic bars 10, can be embodied as respective second ferromagnetic bars 20.

The ferromagnetic bars 10, 20 can each be embodied out of a plurality of transformer sheets that can be electrically isolated to each other. By this configuration, eddy currents can be prevented.

The embodiment of the ferromagnetic cores 125 and the magnetic coupling elements 126 as respective ferromagnetic bars 10, 20 can provide for a good magnetic coupling because there is no gap and even no material junction between cores 125 and magnetic coupling elements 126 within one module.

If the parts of a module as shown in FIG. 1 are concatenated with identical parts of another module, there can remain respective gaps between cores 125 of neighboring modules. For that reason, the ferromagnetic bars 10, 20 can each comprise a contact surface 127 as magnetic coupling enhancer. The contact surfaces 127 can be positioned at the respective lower or bottom sides of the ferromagnetic bars 10, 20. They can be used in order to abut magnetic coupling rods for increased magnetic coupling to neighboring modules. It will be explained further below with reference to FIG. 5 how this can be accomplished.

Figure 2A:
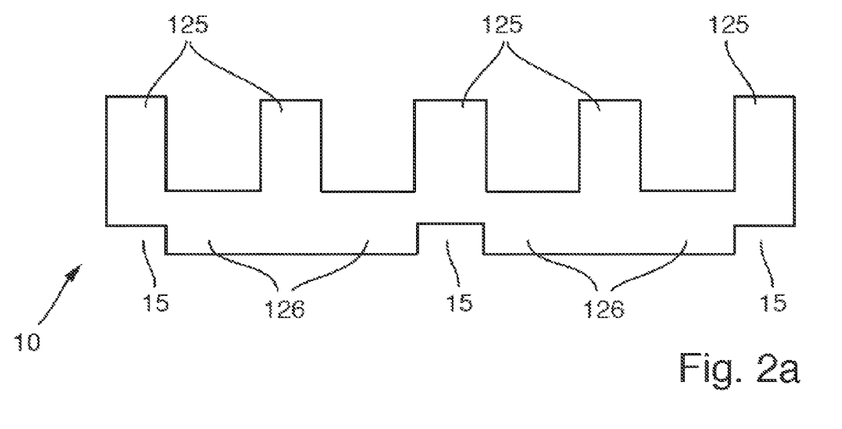
FIG. 2a illustrates a ferromagnetic bar used in the configuration shown in FIG. 1 according to an embodiment of the present disclosure.
Figure 2B:
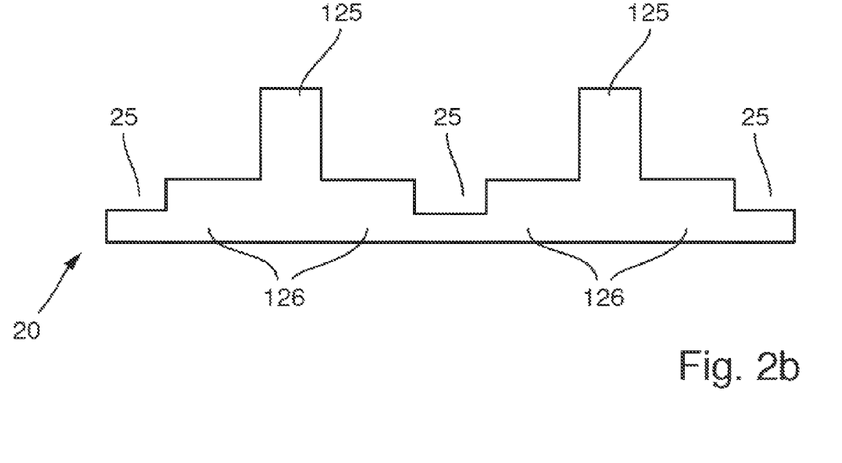
FIG. 2b illustrates another ferromagnetic bar used in the configuration of FIG. 1 according to an embodiment of the present disclosure.

FIG. 2a shows a schematic cross-sectional view of the first ferromagnetic bar 10. FIG. 2b shows a schematic cross-sectional view of the second ferromagnetic bar 20. It can be noted that both FIG. 2a and FIG. 2b depict only parts of a respective ferromagnetic bar 10, 20, wherein the ferromagnetic bars 10, 20 as shown in FIG. 1 are considerably longer.

The first ferromagnetic bar 10 as shown in FIG. 2a can have ferromagnetic cores 125 extending upward. The cores 125 can have a certain distance that can be equal between each two pairs of cores 125. Between each two cores 125, there can be arranged a magnetic coupling element 126.

Below each second core 125, a recess 15 can be formed. The recesses 15 can be arranged at the lower side of the first ferromagnetic bar 10.

The second ferromagnetic bar 20 can also have ferromagnetic cores 125, which can, however, be arranged with twice the distance of the ferromagnetic cores 125 of the first ferromagnetic bar 10 as shown in FIG. 2a. Instead, the second ferromagnetic bar 20 can have recesses 25 formed at its upper side at each second position where the first ferromagnetic bar 10 can have a core 125. The recesses 25 of the second ferromagnetic bar 20 can interact with corresponding recesses 15 of the first ferromagnetic bars 10 such that the first ferromagnetic bars 10 and the second ferromagnetic bars 20 can be arranged as shown in FIG. 1. In particular, they can be arranged such that a plurality of first ferromagnetic bars 10 can be arranged parallel to each other, that a plurality of second ferromagnetic bars 20 can be arranged parallel to each other, and that the first ferromagnetic bars 10 can be arranged perpendicular to the second ferromagnetic bars 20. The recesses 15, 25 can allow for a simple assembly of the configuration as shown in FIG. 1.

Figure 3:
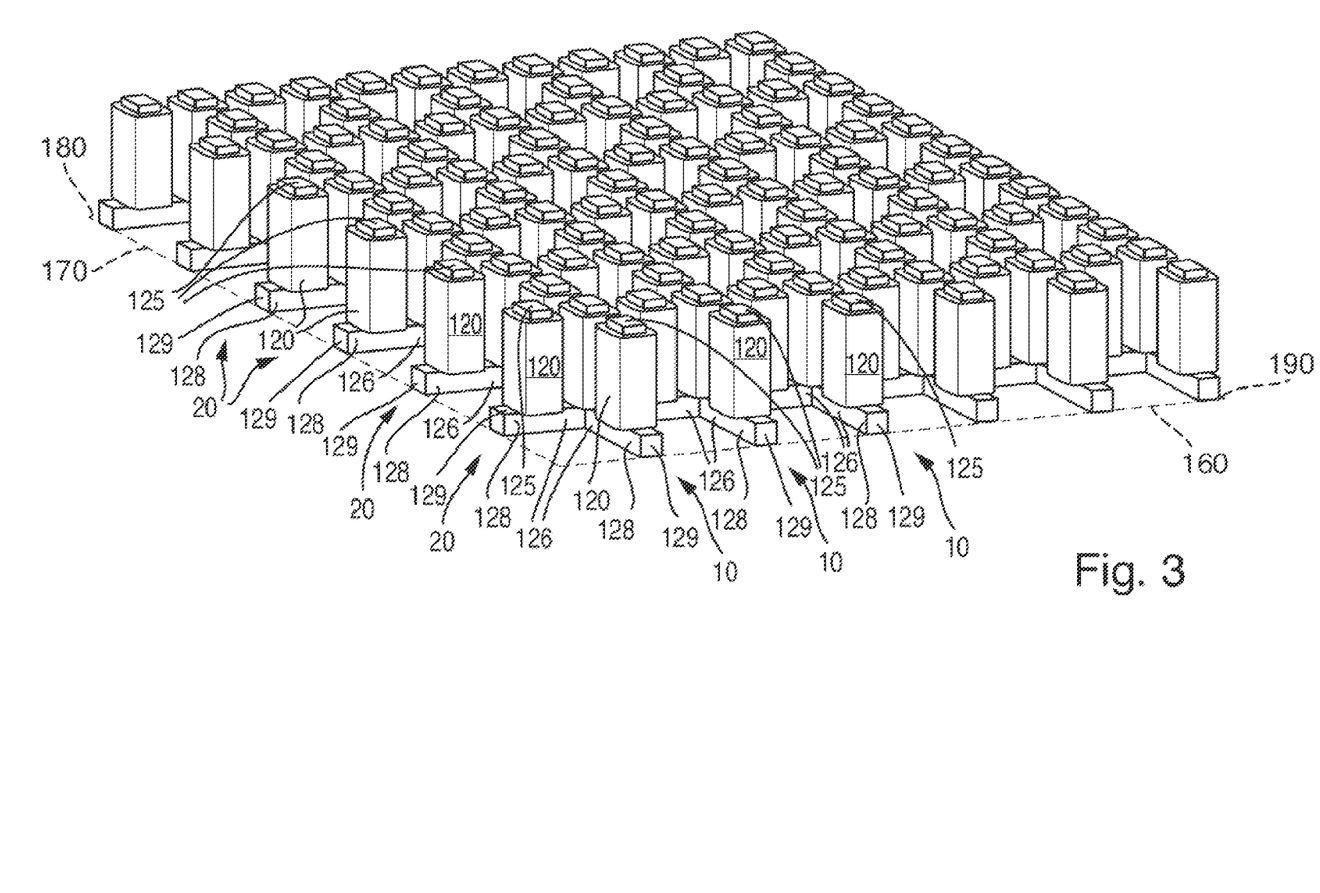
FIG. 3 illustrates a part of a module for a laboratory sample distribution system according to a second embodiment of the present disclosure.

FIG. 3 shows a part of a module for a laboratory sample distribution system according to a second embodiment. This configuration is similar to the configuration according to the first embodiment as shown in FIG. 1. For that reason, only the differences will be discussed in the following. Regarding the other items and features, reference is made to the description of FIG. 1 given above.

In contrast to FIG. 1, the ferromagnetic bars 10, 20 can each comprise a magnetic coupling protrusion 128 between a ferromagnetic core 125 and an outer edge 160, 170, 180, 190 (as depicted by the dashed line) of the module as magnetic coupling enhancers. The outer edges 160, 170, 180, 190 of a module can be the edges determining a border line to another module. The outer edges 160, 170, 180, 190 can be determined by border lines of the transport plane (not shown) of a respective module. The magnetic coupling protrusions 128 can be arranged in line with the magnetic coupling elements 126 between the cores 125. The magnetic coupling protrusions 128 can provide for an increased coupling to ferromagnetic cores 125 of neighboring modules.

Each magnetic coupling protrusion 128 can comprise a magnetic coupling surface 129 positioned at the outer edge (160, 170, 180, 190) of the module and facing towards a surrounding of the module. The magnetic coupling surface 129 can especially face to another magnetic coupling surface of a neighboring module such that a distance between the magnetic coupling surfaces 129 can be minimized. Thus, a gap between the magnetic coupling surfaces 129 can be minimized. Magnetic coupling between neighboring modules can thus be enhanced. By use of the second embodiment shown in FIG. 3, magnetic coupling can be enhanced without a need for additional magnetic coupling rods.

Figure 4:
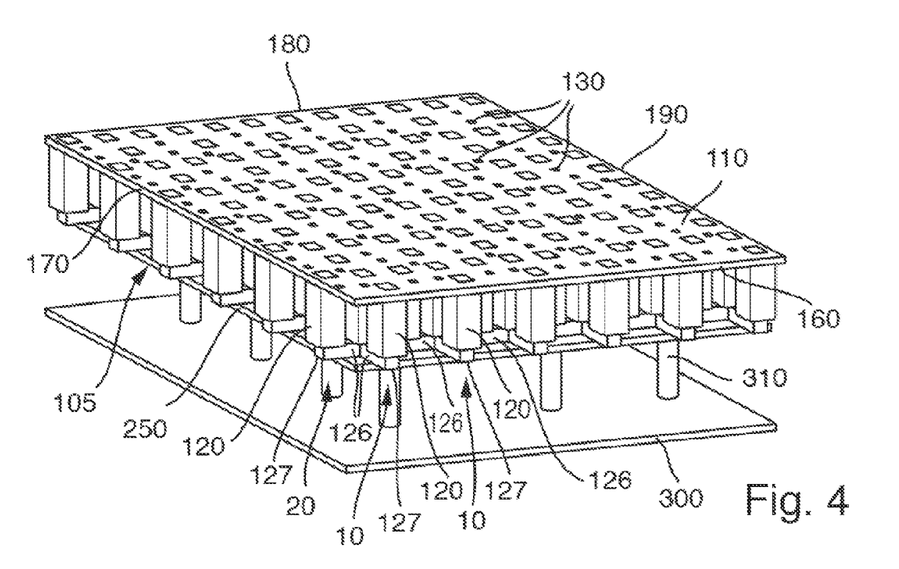
FIG. 4 illustrates a module for a laboratory sample distribution system using the configuration of FIG. 1 according to an embodiment of the present disclosure.

FIG. 4 shows a module 105 for a laboratory sample distribution system, the module 105 comprising a transport plane 110 that can be adapted such that sample container carriers can move on it. Furthermore, a plurality of magnetic sensors 130 can be distributed in the transport plane 110. These magnetic sensors 130 can be used in order to sense respective positions of sample container carriers.

Below the transport plane 110, parts as shown in FIG. 1 can be arranged. Specifically, a plurality of electro-magnetic actuators 120 with respective ferromagnetic cores 125 can be arranged. Between the ferromagnetic cores 125, respective magnetic coupling elements 126 can be arranged. The bars 10, 20 can be supported by a supporting structure 250 of the module 105. The module 105 can be retained with a lower or bottom side of the supporting structure 250 on pillars 310 of a retaining frame 300 of a laboratory sample distribution system. The bottom side of the supporting structure can be opposite to the transport plane 110.

Figure 5:
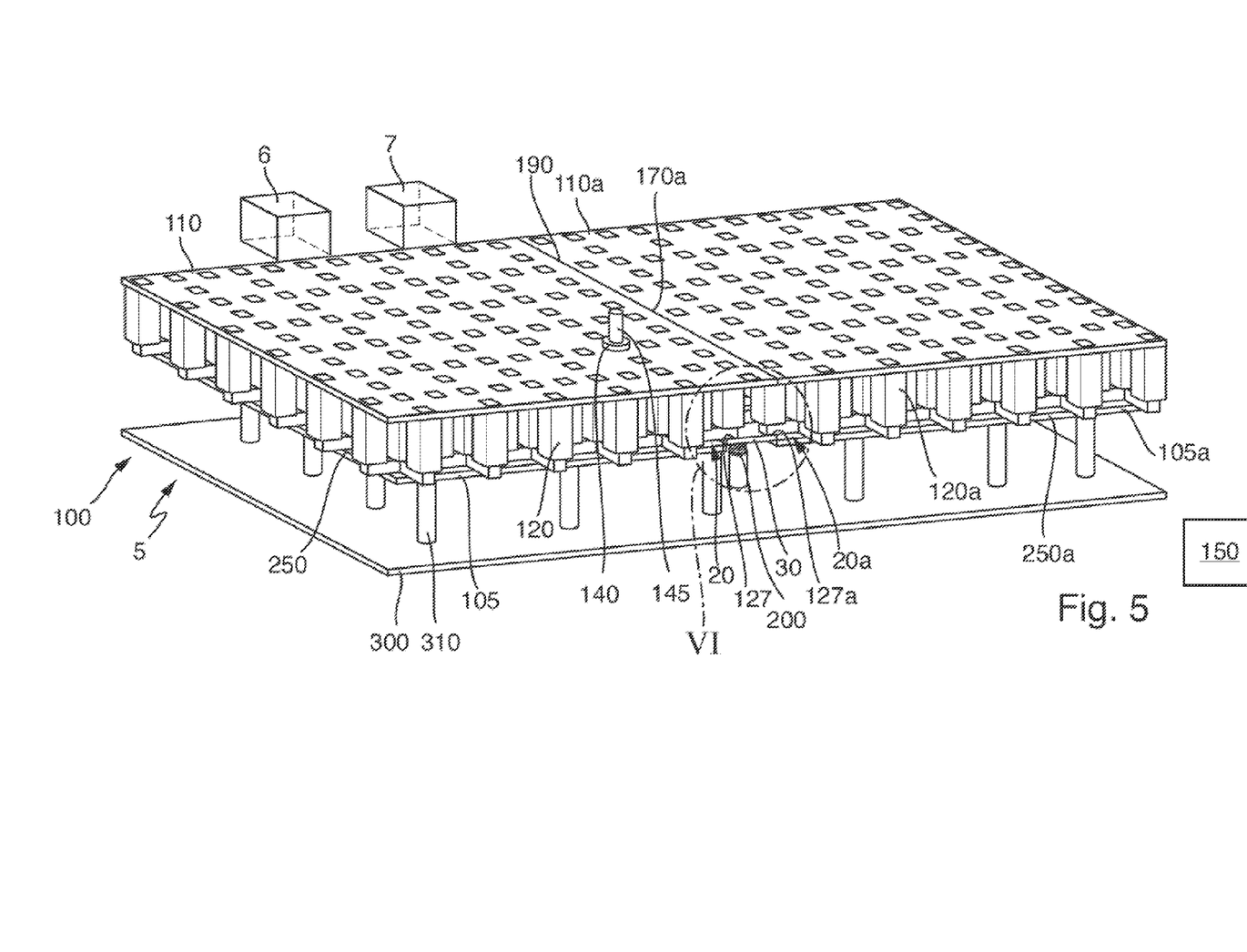
FIG. 5 illustrates a laboratory automation system comprising a laboratory sample distribution system with two modules as shown in FIG. 4 according to an embodiment of the present disclosure.

FIG. 5 shows a laboratory automation system 5 comprising a first laboratory station 6, a second laboratory station 7 and a laboratory sample distribution system 100. The laboratory stations 6, 7 are shown as examples for a plurality of laboratory stations that are typically present in a laboratory automation system. They can, for example, be pre-analytical, analytical and/or post-analytical stations that perform tasks like analyzing a sample, centrifugation of a sample or the like.

The laboratory sample distribution system 100 can comprise a first module 105 and a second module 105a. An outer edge 190 of the first module 105 can touch an outer edge 170a of the second module. The first module 105 and the second module 105a can be concatenated such that they can form a common transport plane. The common transport plane can be formed by the transport plane 110 of the first module 105 and the transport plane 110a of the second module 105a. The first module 105 and the second module 105a can be retained with bottom sides of their supporting structures 250, 250a on pillars 310 of a retaining frame 300 of the laboratory sample distribution system 100. Regarding the further details of the modules 105, 105a, reference is made to FIG. 4 and the corresponding description given above.

In order to enhance coupling between ferromagnetic cores 125, 125a of different modules 105, 105a, magnetic coupling rods 30 can be positioned between respective ferromagnetic bars 20, 20a of different modules 105, 105a. The magnetic coupling rods 30, each having a rectangular cross-section area, can be formed out of magnetically highly permeable material in order to provide for an effective coupling. Each magnetic coupling rod 30 can abut two magnetic coupling surfaces 127, 127a of the different modules 105, 105a. Thus, there can be no remaining gap between neighboring magnetic rods 20, 20a. The arrangement is shown in further detail in FIG. 6, which depicts the encircled part VI of FIG. 5.

Figure 6:
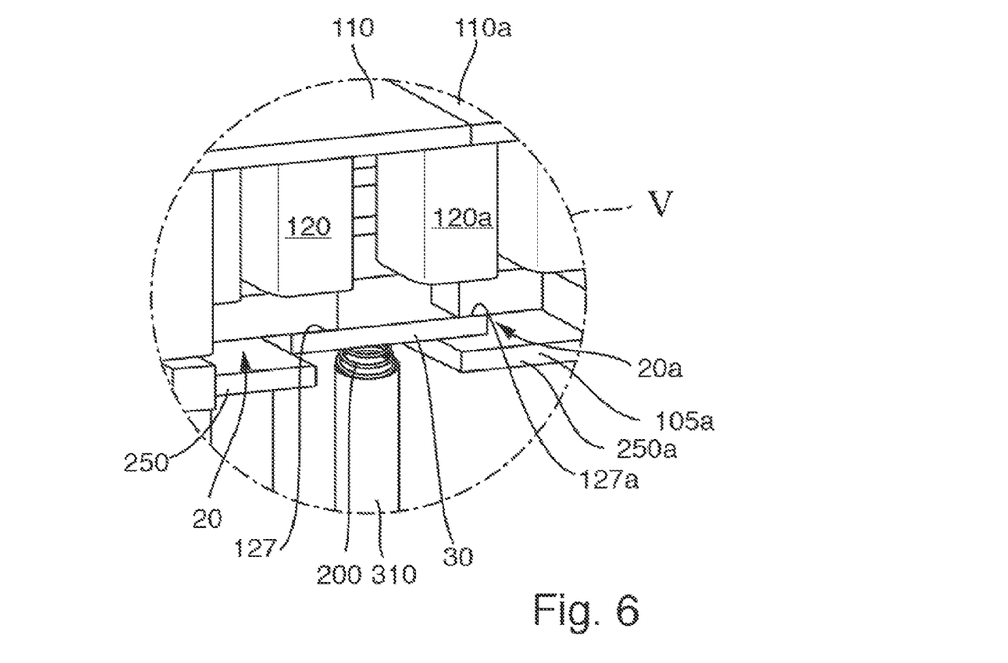
FIG. 6 illustrates a part of the laboratory automation system as shown in FIG. 5 in more detail according to an embodiment of the present disclosure.

This measure can lead to a magnetic coupling between cores 125, 125a of different modules 105, 105a that can be approximately the same as the magnetic coupling between neighboring cores 125 of a module 105 that can be connected by a magnetic coupling element 126.

The magnetic coupling rods 30 can be detachably fixed by a plurality of springs 200 on pillars 310 from the retaining frame 300 to the contact surfaces 127, 127a. This can allow for a simple detaching and attaching of the magnetic coupling rods 30 in the case one of the modules 105, 105a needs to be replaced.

It can be understood that a typical laboratory sample distribution system 100 can comprise more than two modules 105, 105a. Magnetic coupling between a plurality of modules 105, 105a can be enhanced just like described here with respect to two modules 105, 105a.

The laboratory sample distribution system 100 can further comprise a sample container carrier 140. The sample container carrier 140 can carry a sample container 145. The sample container carrier 140 can have a magnetically active device in the form of a permanent magnet that is not shown in FIG. 5. The sample container carrier 140 can move on the common transport plane. The sample container 145 can be embodied as a tube made of transparent plastic material with an opening at its top side and can carry blood samples or other medical samples. By use of the sample container carrier 140, sample containers 145 can be distributed between the laboratory stations 6, 7 and other equipment.

It can be noted that a typical laboratory sample distribution system 100 can comprise more than one sample container carrier 140. The sample container carrier 140 shown in FIG. 5 is given as an exemplary illustration only.

The laboratory sample distribution system 100 can further comprise a control unit 150 that can drive the electro-magnetic actuators 120, 120a such that the sample container carriers 140 can move over the common transport plane on respective transport paths.

Figure 7:
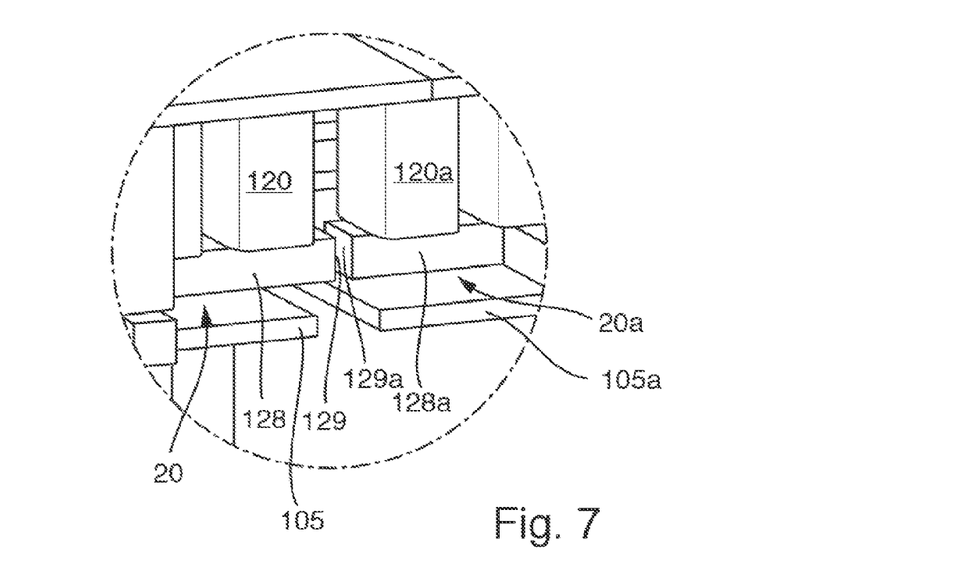
FIG. 7 illustrates a part of a laboratory automation system comprising a laboratory sample distribution system with two modules as one of them shown in part in FIG. 3 according to an embodiment of the present disclosure.

FIG. 7 shows in detail a part of a laboratory automation system comprising a laboratory sample distribution system with two modules 105, 105a, wherein the kind of module 105, 105a is shown in part in FIG. 3. Regarding the further details of the modules 105, 105a, reference is made to FIG. 3 and the corresponding description given above. The configuration of FIG. 7 can be similar to the configuration according to the first embodiment as shown in FIG. 6. For that reason, only the differences will be discussed in the following. Regarding the other items and features, reference is made to the description of FIG. 6 given above.

In contrast to FIG. 6, the ferromagnetic bars 20, 20a can each comprise a magnetic coupling protrusion 128, 128a. Each magnetic coupling protrusion 128, 128a can comprise a magnetic coupling surface 129, 129a and facing towards the other such that a distance between the magnetic coupling surfaces 129 can be minimized. Thus, a gap between the magnetic coupling surfaces 129 can be minimized. Magnetic coupling between neighboring 105, 105a modules can be thus enhanced.

By use of the second embodiment shown in FIG. 7, magnetic coupling can be enhanced without a need for additional magnetic coupling rods. However, additionally, magnetic coupling rods can be provided as shown in FIGS. 5 and 6 and described above. Additionally, each magnetic coupling surface may have a cross-section area larger than a cross-section area of the magnetic coupling elements 126.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A module for a laboratory sample distribution system, the module comprising:
   a transport plane to support sample container carriers, each sample container carrier comprising at least one magnetically active device;
   a plurality of electro-magnetic actuators stationary arranged below the transport plane, the electro-magnetic actuators move the sample container carriers on top of the transport plane by applying a magnetic force to the sample container carriers, wherein each electro-magnetic actuator comprises a ferromagnetic core, wherein adjacent ferromagnetic cores are magnetically coupled to each other by respective magnetic coupling elements; and
   a magnetic coupling enhancer for increasing magnetic coupling to adjacent modules, the magnetic coupling enhancer comprises,
      a plurality of magnetic coupling protrusions, each magnetic coupling protrusion positioned between an outer edge of the module and a corresponding ferromagnetic core of an electro-magnetic actuator positioned adjacent to the outer edge, wherein each magnetic coupling protrusion comprises a magnetic coupling surface positioned at an outer edge of the module facing towards a surrounding of the module, and wherein the magnetic coupling surfaces are arranged to magnetically couple to a further magnetic coupling surface of a neighbouring module, and a plurality of contact surfaces, the contact surfaces are to be contacted by a corresponding number of magnetic coupling rods.

2. The module according to claim 1, wherein each magnetic coupling surface has a cross-section area larger than a cross-section area of the magnetic coupling elements.

3. The module according to claim 1, further comprising,
a plurality of positions defined on the module in a chequered manner, wherein each electro-magnetic actuator is located on one such position such that in each second line of positions each second position is left blank.

4. The module according to claim 3, wherein the module has four outer edges forming a rectangular shape, wherein electro-magnetic actuators are located on each position along two of the four edges that are located perpendicular to each other, and wherein electro-magnetic actuators are located on each second position along two further edges of the four edges.

5. The module according to claim 3, wherein the ferromagnetic cores, the magnetic coupling elements between those ferromagnetic cores, and the magnetic coupling enhancers of each line of positions having no blanks are formed as a single ferromagnetic bar.

6. The module according to claim 5, further comprises,
a first set of ferromagnetic bars and a second set of ferromagnetic bars, wherein the ferromagnetic bars of the first set is parallel to each other and the ferromagnetic bars of the second set is parallel to each other, and the ferromagnetic bars of the first set is perpendicular to the ferromagnetic bars of the second set.

7. The module according to claim 6, wherein the ferromagnetic bars each have recesses arranged such that the recesses of the ferromagnetic bars of the first set are complementary to the recesses of the ferromagnetic bars of the second set.

8. The module according to claim 7, wherein the ferromagnetic bars are arranged such that corresponding complementary recesses abut each other.

9. The module according to claim 5, wherein the ferromagnetic bars are each formed out of a transformer.

10. The module according to claim 5, wherein the ferromagnetic bars are each formed out of a group of parallel transformer sheets electrically isolated to each other.

11. The module according to claim 9, wherein the ferromagnetic cores, the magnetic coupling elements, the magnetic coupling enhancement means, the ferromagnetic bars, and/or the transformer sheets are formed out of magnetically permeable material.

12. A laboratory sample distribution system, the laboratory sample distribution system comprising:
a plurality of sample container carriers to carry one or more sample containers, each sample container carrier comprising at least one magnetically active device;
a plurality of modules according to claim 1, wherein the modules are arranged adjacent to each other such that magnetic coupling protrusions of neighbouring modules face each other and that the transport planes of the modules form a common transport plane to support the sample container carriers; and
a control device to control the movement of the sample container carriers on top of the common transport plane by driving the electro-magnetic actuators of the modules such that the sample container carriers move along corresponding transport paths.

13. A laboratory sample distribution system, the laboratory sample distribution system comprising:
a plurality of sample container carriers to carry one or more sample containers, each sample container carrier comprising at least one magnetically active device;
a plurality of modules according to claim 1, wherein the modules are arranged adjacent to each other such that the transport planes of the modules form a common transport plane to support the sample container carriers;
a plurality of magnetic coupling rods positioned and fixed between two neighbouring contact surfaces of respective different modules; and
a control device to control the movement of the sample container carriers on top of the common transport plane by driving the electro-magnetic actuators of the modules such that the sample container carriers move along corresponding transport paths.

14. The laboratory sample distribution system according to claim 13, further comprising,
a retaining frame, wherein the retaining frame retains the plurality of modules from a bottom side of the modules.

15. The laboratory sample distribution system according to claim 14, wherein the plurality of magnetic coupling rods is detachably fixed to the contact surfaces by a plurality of springs extending from the retaining frame to the magnetic coupling rods such that a spring force is applied to the magnetic coupling rods.

16. The laboratory sample distribution system according to claim 13, wherein each magnetic coupling rod has a rectangular cross-section.

17. A laboratory automation system, the laboratory automation system comprising:
a plurality of laboratory stations; and
a laboratory sample distribution system according to claim 9 to distribute sample containers and/or sample container carriers between the stations.

18. The laboratory automation system according to claim 17, wherein the plurality of laboratory stations comprises pre-analytical, analytical and/or post-analytical stations.

* * * * *